US008116430B1

(12) United States Patent
Shapiro et al.

(10) Patent No.: US 8,116,430 B1
(45) Date of Patent: *Feb. 14, 2012

(54) MULTI-MODE CONE BEAM CT RADIOTHERAPY SIMULATOR AND TREATMENT MACHINE WITH A FLAT PANEL IMAGER

(75) Inventors: Edward G. Shapiro, Menlo Park, CA (US); Edward J. Seppi, Portola Valley, CA (US); John M. Pavkovich, Palo Alto, CA (US); Peter Munro, Mountain View, CA (US); Stanley W. Johnsen, Palo Alto, CA (US); Richard E. Colbeth, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/891,505

(22) Filed: Aug. 10, 2007

Related U.S. Application Data

(63) Continuation of application No. 10/324,227, filed on Dec. 18, 2002.

(51) Int. Cl.
*A61N 5/10* (2006.01)
*H05G 1/64* (2006.01)
*A61B 6/03* (2006.01)

(52) U.S. Cl. ............. 378/65; 378/19; 378/196; 378/197

(58) Field of Classification Search ............. 378/9, 19, 378/65, 20
See application file for complete search history.

(56) References Cited

U.S. PATENT DOCUMENTS

| 3,133,227 A | 5/1964 | Brown et al. |
| 3,144,552 A | 8/1964 | Schonberg |
| 3,193,717 A | 7/1965 | Nunan |
| 4,149,247 A | 4/1979 | Pavkovich et al. |
| 4,149,248 A | 4/1979 | Pavkovich |
| 4,208,675 A | 6/1980 | Bajon et al. |
| 4,209,706 A | 6/1980 | Nunan |
| 4,521,808 A | 6/1985 | Ong et al. |
| 4,593,967 A | 6/1986 | Haugen |
| 4,675,731 A | 6/1987 | Takasu et al. |
| 4,679,076 A | 7/1987 | Vikterlof et al. |
| 4,726,046 A | 2/1988 | Nunan |

(Continued)

FOREIGN PATENT DOCUMENTS

DE 4223488 A1 1/1994

(Continued)

OTHER PUBLICATIONS

Ning et al., "Flat Panel Detector-Based Cone-Beam Volume CT Angiography Imaging: System Evaluation," IEEE Transactions on Medical Imaging, vol. 19, No. 9, Sep. 2000, 949-963.*

(Continued)

*Primary Examiner* — Allen C. Ho
(74) *Attorney, Agent, or Firm* — Blakely, Sokoloff, Taylor & Zafman LLP

(57) ABSTRACT

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

20 Claims, 4 Drawing Sheets

Simulator kV Cone Beam CT Diagram

U.S. PATENT DOCUMENTS

| | | | |
|---|---|---|---|
| 4,741,621 | A | 5/1988 | Taft et al. |
| 4,825,393 | A | 4/1989 | Nishiya |
| 4,853,777 | A | 8/1989 | Hupp |
| 4,868,844 | A | 9/1989 | Nunan |
| 5,014,292 | A | 5/1991 | Siczek et al. |
| 5,027,818 | A | 7/1991 | Bova et al. |
| 5,039,867 | A | 8/1991 | Nishihara et al. |
| 5,080,100 | A | 1/1992 | Trotel |
| 5,099,505 | A | 3/1992 | Seppi et al. |
| 5,117,445 | A | 5/1992 | Seppi et al. |
| 5,168,532 | A | 12/1992 | Seppi et al. |
| 5,247,555 | A | 9/1993 | Moore et al. |
| 5,262,649 | A | 11/1993 | Antonuk et al. |
| 5,335,255 | A | 8/1994 | Seppi et al. |
| 5,394,452 | A | 2/1995 | Swerdloff et al. |
| 5,438,991 | A | 8/1995 | Yu et al. |
| 5,471,546 | A | 11/1995 | Meier |
| 5,537,452 | A | 7/1996 | Shepherd et al. |
| 5,661,773 | A * | 8/1997 | Swerdloff et al. .............. 378/65 |
| 5,692,507 | A | 12/1997 | Seppi et al. |
| 5,751,781 | A | 5/1998 | Brown et al. |
| 5,949,811 | A | 9/1999 | Baba et al. |
| 5,956,382 | A | 9/1999 | Wiener-Avnear et al. |
| 5,999,587 | A | 12/1999 | Ning et al. |
| 6,031,888 | A | 2/2000 | Ivan et al. |
| 6,041,097 | A | 3/2000 | Roos et al. |
| 6,104,778 | A | 8/2000 | Murad |
| 6,104,780 | A | 8/2000 | Hanover et al. |
| 6,144,875 | A | 11/2000 | Schweikard et al. |
| 6,219,403 | B1 | 4/2001 | Nishihara |
| 6,222,901 | B1 | 4/2001 | Meulenbrugge et al. |
| 6,292,526 | B1 | 9/2001 | Patch |
| 6,307,914 | B1 | 10/2001 | Kunieda et al. |
| 6,325,537 | B1 | 12/2001 | Watanabe |
| 6,325,758 | B1 | 12/2001 | Carol et al. |
| 6,370,421 | B1 | 4/2002 | Williams et al. |
| 6,381,302 | B1 | 4/2002 | Berestov |
| 6,385,286 | B1 | 5/2002 | Fitchard et al. |
| 6,385,288 | B1 | 5/2002 | Kanematsu |
| 6,429,578 | B1 | 8/2002 | Danielsson et al. |
| 6,463,122 | B1 | 10/2002 | Moore |
| 6,480,565 | B1 | 11/2002 | Ning |
| 6,508,586 | B2 | 1/2003 | Oota |
| 6,590,953 | B2 * | 7/2003 | Suzuki et al. .................... 378/15 |
| 6,661,870 | B2 | 12/2003 | Kapatoes et al. |
| 6,744,848 | B2 | 6/2004 | Stanton et al. |
| 6,842,502 | B2 * | 1/2005 | Jaffray et al. .................... 378/65 |
| 6,865,254 | B2 | 3/2005 | Nafstadius |
| 6,888,919 | B2 | 5/2005 | Graf |
| 6,914,959 | B2 | 7/2005 | Bailey et al. |
| 2001/0001807 | A1 | 5/2001 | Green |
| 2001/0008271 | A1 | 7/2001 | Ikeda et al. |
| 2002/0066860 | A1 | 6/2002 | Possin |
| 2003/0007601 | A1 | 1/2003 | Jaffray et al. |

FOREIGN PATENT DOCUMENTS

| | | |
|---|---|---|
| DE | 19614643 A1 | 10/1997 |
| EP | 0062941 B1 | 9/1984 |
| EP | 0205720 A1 | 12/1986 |
| EP | 0480035 B1 | 11/1994 |
| EP | 0948930 | 10/1999 |
| FR | 2 269 745 | 11/1975 |
| FR | 2 551 664 | 3/1985 |
| GB | 1328033 | 8/1973 |
| JP | 63294839 | 12/1988 |
| JP | 5057028 | 3/1993 |
| WO | WO 85/03212 A1 | 8/1985 |
| WO | WO 9014129 | 11/1990 |
| WO | WO 9200567 | 1/1992 |
| WO | WO 9220202 | 11/1992 |
| WO | WO 0160236 | 8/2001 |
| WO | WO 0213907 | 2/2002 |

OTHER PUBLICATIONS

Ning et al., "Flat Panel Detector-Based Cone-Beam Volume CT Angiography Imaging: System Evaluation," IEEE Transactions on Medical Imaging, vol. 19, No. 9, Sep. 2000, 949-963.

Ning et al., SPIE vol. 3659, 192-203, 1999.

Jaffray et al., "Flat-Panel Cone-Beam Computed Tomography for Image-Guided Radiation Therapy," Int. J. Radiation Oncology Biol. Phys., vol. 53, No. 5 (2002), pp. 1337-1349.

Jaffray et al., SPIE vol. 3659, 204-214, 1999.

Siewerdsen et al., Med. Phys. 26, 2635-2647, 1999.

Siewerdsen et al., Med. Phys. 26, 1624-1641, 1999.

Hara et al., "Radiotherapeutic System," 00480035/EP-B1, Citation from World Patent, 1994, 1 page.

"Advanced Workstation for Irregular Field Simulation and Image Matching," Copyright 1999, MDS Nordion, 7 pages.

Ragan, "Correction for Distortion in a Beam Outline Transfer Device in Radiotherapy CT-Based Simulation," Med. Phys. 20 (1), Jan./Feb. 1993, pp. 179-185.

Kushima, GJ et al., "New development of integrated CT simulation system for radiation therapy planning," Abstract. Kobe J. Med. Sci., Dec. 1993, vol. 39, No. 5-6, pp. 17-213.

Kutcher, et al., "Three dimensional radiation treatment planning," Abstract (1998), Dosimetry in radiotherapy, vol. 2, Proceedings of an international symposium held in Vienna, Austria, Aug.-Sep. 1987.

Mohan, et al., "Intersection of shaped radiation beams with arbitrary image sections," Abstract, Comput Methods Programs Biomed, Jun. 1987, vol. 24, pp. 161-168.

Ning, et al., "Image intensifier-based volume tomographic angiography imaging system: system evaluation," SPIE, Medical Imaging 1995, vol. 2432, pp. 280-290.

Redpath, et al., "Use of a simulator and treatment planning computer as a CT scanner for radiotherapy planning," Abstract, Proceedings—Eighth International Conference on the Use of Computers in Radiation Therapy held in Toronto, Canada, 1984, pp. 281-287. IEEE, New York, NY.

Reynolds, et al., "An algorithm for three-dimensional visualization of radiation therapy beams," Abstract, Med Phys, Jan.-Feb. 1988, vol. 15 (1), pp. 24-28.

Andrew, et al., "A video-based patient contou acquisition system for the design radiotherapy compensators," Abstract, Med Phys, May-Jun. 1989, vol. 16 (3), pp. 425-430.

Brewsterfuauf, et al., "Automatic generation of beam apertures," Abstract, Medical Physics, 1993, vol. 20, pp. 1337, 1342.

Elliott, et al., "Interactive imagine segmentation for radiation treatment planning," Abstract, IBM Systems Journal, 1992, vol. 31, No. 4, pp. 620-634.

Gademann, et al., "Three-dimensional radiation planning. Studies on clinical integration," Abstract, Strahlenther Onkol, 1993, vol. 169 (3), pp. 159-167.

Jaffray, et al., "Cone-beam CT: applications in image-guided external beam radiotherapy and brachytherapy," Engineering in Medicine and Biology Society, Proceedings of the 22nd Annual International Conference of the IEEE, Jul. 2000, vol. 3, P. 2044.

Masahiro et al., "Patient Beam Positioning System Using CT Images", Phys. Med. Biol., 1982, vol. 27, No. 2, pp. 301-305, printed in Great Britain.

Balter, James M. et al., "Daily Targeting of Intrahepatic Tumors for Radiotherapy," Int. J. Radiation Oncology Biol. Phys., vol. 52, No. 1 (2002), pp. 266-271.

Kudo et al., "Feasible cone beam scanning methods for exact reconstruction in three-dimensional tomography," J. Opt. Soc. Am. A; 7, 2169 (1990).

Rizo et al., "Comparison of two three-dimensional x-ray cone-beam-reconstruction algorithms with circular source trajectories," J. Opt. Soc. Am. A, 10, 1639 (1991).

Yan et al., "Derivation and analysis of a filtered backprojection algorithm for cone beam projection," IEEE Trans. Medical Imaging, 10, 462 (1991).

Midgley, S. et al., "A Feasibility Study for Megavoltage Cone Beam CT Using A Commercial EPID," Phys. Med. Biol., vol. 43 (1998), pp. 155-169.

Uematsu, Minoru, M.D. et al, "Intrafractional Tumor Position Stability During Computed Tomography (CT)-Guided Frameless Stereotactic Radiation Therapy for Lung or Liver Cancers With a Fusion of CT and Linear Accelerator (FOCAL) Unit," Int. J. Radiation Oncology Biol. Phys., vol. 48, No. 2 (2000), pp. 443-448.

Mosleh-Shirazi, Mohammad Amin et al., "A Cone-Beam Megavoltage CT Scanner for Treatment Verification in Conformal Radiotherapy," Radiotherapy and Oncology, vol. 48 (1998), pp. 319-328.

Jaffray, David A., Ph.D. et al., "A Radiographic and Tomographic Imaging System Integrated Into a Medical Linear Accelerator for Localization of Bone and Soft-Tissue Targets," Int. J. Radiation Oncology Biol. Phys., vol. 45, No. 3 (1999), pp. 773-789.

Cho, Paul S. et al., "Cone-Beam CT for Radiotherapy Applications," Phys. Med. Biol., vol. 40 (1995), pp. 1863-1883.

Keys, D, "A CCTV-microcomputer biostereometric system for use in radiation therapy (topography, medical physics, tissue compensators)," Abstract, Energy Science and Technology, 1984, vol. 45-12B, pp. 3857.

Kuhn, MH, "AIM Project A2003: COmputer VIsion in RAdiology (COVIRA)," Abstract, Computer Methods and Programs in Biomedicine, Oct. 1994, vol. 45, No. 1-2, pp. 17-31.

Pisani, Laura, M.S. et al., "Setup Error in Radiotherapy: On-line Correction Using Electronic Kilovoltage and Megavoltage Radiographs," Int. J. Radiation Oncology Biol. Phys., vol. 47, No. 3 (2000), pp. 825-839.

Siewerdsen, Jeffery H. and Jaffray, David A., "Cone-Beam Computed Tomography With a Flat:Panel Imager: Magnitude and Effects of X-Ray Scatter," Med. Phys., vol. 28, No. 2, Feb. 2001, pp. 220-231.

Feldkamp, L.A. et al. "Practical Cone-Beam Algorithm," J. Opt. Soc. Am. A., vol. 1, No. 6, Jun. 1984; pp. 612-619.

Drake, D.G. et al, "Characterization of a Fluoroscopic Imaging System for kV and MV Radiography," Med. Phys., vol. 27, No. 5, May 2000, pp. 898-905.

Jaffray, D.A. and Siewerdsen, J.H., "Cone-Beam Computed Tomography with a Flat-Panel Imager: Initial Performance Characterization," Med. Phys., vol. 27, No. 6, Jun. 2000, 1311-1323.

Fahrig, R. and Holdsworth, D. W., "Three-Dimensional Computed Tomographic Reconstruction Using a C-Arm Mounted XRII: Image Based Correction of Gantry Motion Nonidealities," Med. Phys., vol. 27, No. 1, Jan. 2000, pp. 30-38.

Siewerdsen, Jeffery H. and Jaffray, David A., "Optimization of X-Ray Imaging Geometry (With Specific Application to Flat-Panel Cone-Beam Computed Tomography)," Med. Phys., vol. 27, No. 8, Aug. 2000, pp. 1903-1914.

Nakagawa, Keiichi, M.D. et al., "Megavoltage CT-Assisted Stereotactic Radiosurgery for Thoracic Tumors: Original Research in the Treatment of Thoracic Neoplasms," Int. J. Radiation Oncology Biol. Phys., vol. 48, No. 2, (2000), pp. 449-457.

Uematsu, Minoru, M.D. et al., "A Dual Computed Tomography Linear Accelerator Unit for Stereotactic Radiation Therapy: A New Approach Without Cranially Fixated Stereotactic Frames," Int. J. Radiation Oncology Biol. Phys., vol. 35, No. 3 (1996), pp. 587-592.

Swindell, William et al., "Computed Tomography With a Linear Accelerator With Radiotherapy Applications," Med. Phys., vol. 10, No. 4, Jul./Aug. 1983; pp. 416-420.

Ruchala, K.J. et al., "Megavoltage CT on a Tomotherapy System," Phys. Med. Biol., vol. 44 (1999), pp. 2597-2621.

Groh, B.A. et al., "A Performance Comparison of Flat-Panel Imager-Based MV and kV Conebeam CT," Med. Phys., vol. 29, No. 6, Jun. 2002, pp. 967-975.

Uematsu, Minoru et al., "Daily Positioning Accuracy of Frameless Stereotactic Radiation Therapy With a Fusion of Computed Tomography and Linear Accelerator (FOCAL) Unit: Evaluation of Z-Axis With a Z-Marker," Radiotherapy and Oncology, vol. 50, No. 3, Mar. 1999, pp. 337-339.

Supplementary European Search Report mailed Jan. 12, 2011; EP Appln No. 03786979.9; 3 pages.

* cited by examiner

Figure 1 - Simulator kV Cone Beam CT Diagram

Figure 3- MV Cone Beam CT Diagram

MULTI-MODE CONE BEAM CT RADIOTHERAPY SIMULATOR AND TREATMENT MACHINE WITH A FLAT PANEL IMAGER

CROSS-REFERENCE TO RELATED APPLICATIONS

This application is a continuation of U.S. patent application Ser. No. 10/324,227 filed Dec. 18, 2002.

TECHNICAL FIELD

The present invention pertains in general to therapeutic radiology. In particular, the invention involves imaging devices.

BACKGROUND

An objective of radiation therapy is to maximize the amount of radiation to a target volume (e.g., a cancerous tumor) and minimize the amount of radiation to healthy tissues and critical structures. The process of identifying the precise location of the target volume immediately prior to a dose of therapeutic radiation is key to the objective. Since each patient is treated over 30 to 40 fractionated sessions, then the time allowed for each session is relatively short, e.g. 10 to 15 minutes, so the process must be fast as well as accurate.

In the case of electronic portal imaging, megavolt therapeutic X-rays emerging from the patient can be used to generate images. However, this method of target location generates images of low contrast and quality, in addition to incidentally damaging healthy tissue. As a result, imaging with megavoltage (MV) radiation is used primarily for portal verification, that is, to confirm that the treatment volume is being radiated.

Radiotherapy simulator machines have been used to perform the pre-treatment analysis of the target volume before a radiotherapy treatment machine applies the therapeutic radiation. However, traditional radiotherapy simulator machines use bulky image intensifier tube detectors to capture images of the treatment volume. These image intensifier tube detectors have the disadvantage of being very large relative to their imaging area. They also have image spatial distortions from their spherical shaped input surface and the orientation of the intensifier tube with the Earth's magnetic field.

SUMMARY OF AN EMBODIMENT OF THE INVENTION

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

BRIEF DESCRIPTION OF THE DRAWINGS

The present invention is illustrated by way of example and not limitation in the figures of the accompanying drawings, in which like references indicate similar elements and in which.

DETAILED DESCRIPTION

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in gross form rather than in detail in order to avoid obscuring the present invention. These embodiments are described in sufficient detail to enable those skilled in the art to practice the invention, and it is to be understood that other embodiments may be utilized and that logical, mechanical, electrical, and other changes may be made without departing from the scope of the present invention.

A clinical therapy simulation machine having a cone-beam computed tomograpy (CT) radiation source and a flat-panel imager is described. The clinical therapy simulation machine is capable of manipulating the flat-panel imager and the cone beam CT radiation source to generate x-ray images for determining patient setup/alignment and a clinical treatment plan to be implemented by a clinical treatment machine.

Figure 1:
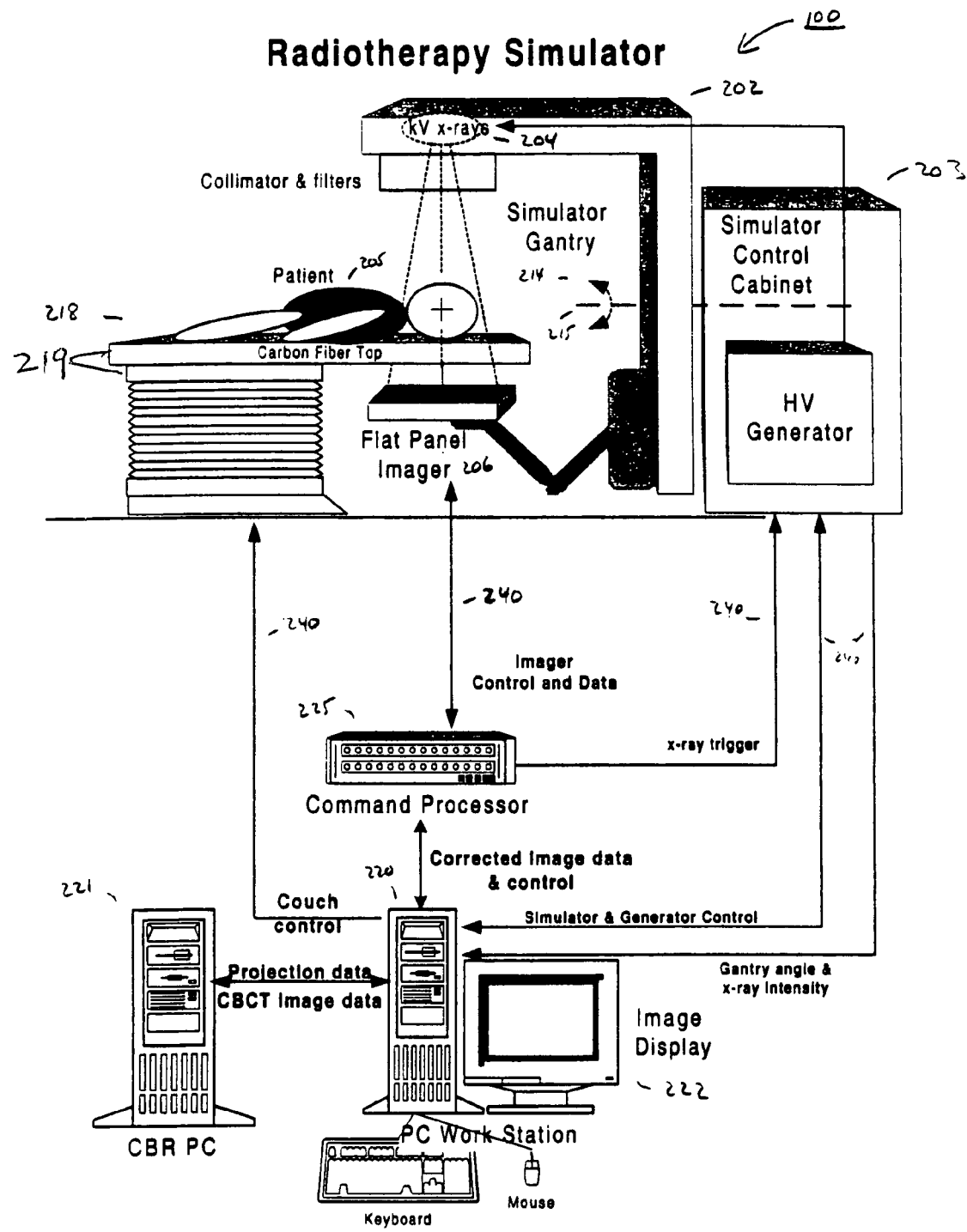
FIG. 1 is an illustration of a side view of one embodiment of a simulation treatment machine.

FIG. 1 is a side view of one embodiment of a simulation treatment machine 100. The simulation treatment machine 100 includes a rotatable gantry 202 pivotably attached to a drive stand 203. A cone-beam CT radiation source 204 and a flat panel imager 206 oppose each other and are coupled to the rotatable gantry 202. In one embodiment, the cone-beam CT radiation source is a kilovoltage radiation source generally in the 50 to 150 kilovolt (kV) energy range, and for example at 125 kilovolts peak (kVp).

A treatment couch 218 is positioned adjacent to the gantry 202 to place the patient and the target volume within the range of operation for the radiation source 204 and the imager 206. The couch 218 may be connected to the therapy simulator rotatable gantry via a communications network and is capable of translating in multiple planes plus angulation for positioning and re-positioning the patient 205 and therefore the target volume.

The gantry 202 can rotate 214 about an isocenterline 215 to place the radiation source 204 and imager 206 at any position 360 degrees around the target volume, for example, to generate CT scan image data. As will be described, cone-beam CT image data can be used to generate a three-dimensional representation of the patient anatomy and the target volume. The image data may further be used to generate a treatment plan to tailor a dose of therapeutic radiation to the target volume.

Figure 2:
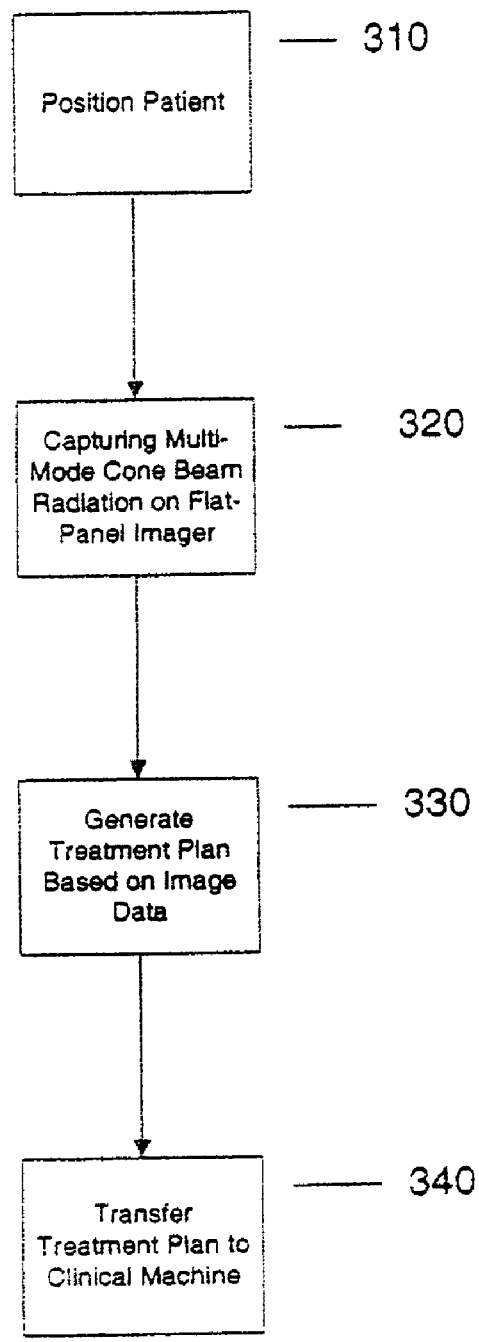
FIG. 2 is an illustration of a process flow of one embodiment of a method for generating a treatment plan.

FIG. 2 is a process diagram of one embodiment of a method for generating a treatment plan. At block 310, a patient is placed on the treatment couch 218 and the couch 218 positioned relative to the simulation machine 100. At block 320, the gantry 202 rotates around the patient 205 while the radiation from the cone-beam CT radiation source 204 impinges the flat-panel imager 206. The gantry 202 rotates and collects image data until a computer can calculate a representation of the patient and the target volume. For example, software in a computer may take the image data to generate cone-beam CT volumetric image data for generation of a treatment plan. At block 330, a treatment plan may be generated from the collected image data. The treatment plan may then be transferred, at block 340, to a clinical treatment machine to provide instructions to the clinical treatment machine, for example, to position a therapeutic radiation source to apply a radiation dose to a target volume, and to minimize dose to health tissue and critical structures.

In one embodiment the flat panel imager 206 is a real-time digital x-ray imager incorporating a large-area amorphous silicon sensor array with a high-sensitivity cesium iodide (CsI) scintillator. The flat panel imager may include a receptor module that incorporates the amorphous silicon sensor array, which accepts incoming X-ray photons and converts them to a digital video signal. The X-ray to light conversion may be provided by a thin or thick columnar CsI:Tl (cesium iodide: thalium doped) scintillator The scintillator may be vacuum deposited in a thin (e.g. 0.6 mm) layer or include individual CsI crystals (e.g., being approximately 9 mm thick with an approximate 0.38 mm×0.38 mm pixel pitch) supported in a housing with an aluminum window (e.g., approximately 1 mm thick). The top of the thin CsI scintillator may be coated with a reflective powder/epoxy mixture. Five sides of each thick crystal may be coated with a reflecting powder/epoxy mixture. The sixth side may be in contact with and face the flat-panel sensor. Alternatively, the scintillator components may have other dimensions.

The receptor module may also include a power supply module (e.g., 24 VDC power), interconnecting cables (e.g., fiber optic control and data cables), and drive and readout circuits followed by digital data conversion and transmission capabilities well known to those of ordinary skill in the art.

It should be appreciated that the flat panel imager may be a two-dimensional large flat panel imager that can operate, for example, at 15 to 30 frames per second (fps) over a wide range of dose. In this way, fluoroscopic, radiographic and cone-beam CT imaging can all be achieved with the same flat panel system. Typically, 300-900 projections may be collected during a single rotation of the gantry depending on the image resolution and dose requirements. Fewer projections allow for a faster collection of cone-beam CT image data (e.g., in 20 to 40 seconds depending on gantry speed limits), thereby, allowing for lower dose cone-beam CT images with less patient motion artifacts. Alternatively, the images may operate at other frame rates.

In one embodiment, the flat panel imager has a landscape orientation, an active area of 39.7×29.8 cm$^2$ with 194 micron pixel pitch, and a pixel count of 2048×1536 pixels. It can operate at a frame rate of 7.5 fps in full resolution mode and at a frame rate of 30 fps in 2×2 binned mode—where the pixel count is reduced to 1024×768 pixels$^2$. For example, the flat panel imager may be an amorphous silicon (a-Si) imager available from Varian Medical Systems of Palo Alto, Calif., under the tradename PaxScan™ 4030A. The PaxScan™ 4030A detectors are each 40 cm×30 cm. The detectors may be coupled to signal processing circuitry comprising a preamplifier stage with dynamically controllable signal gain, as described in U.S. Pat. No. 6,486,808, filed on Oct. 16, 2001, assigned to the assignee of the present invention and incorporated by reference, herein, to improve contrast resolution and dynamic range.

The readout electronics may also be located out of the path of the primary cone-beam CT radiation source 204. The flat panel imager 206 may also employ a split data-line where the top half of the array and the bottom half of the array are read out simultaneously. This allows the imager 206 to read out more rapidly and reduces the parasitic capacitance of the data-lines, which in turn reduces the noise gain of the readout charge amplifiers. It should be appreciated that only half of the frame time is used to read out the pixels. During the rest of the frame time, the sensor can be irradiated without generating any interference patterns due to the pulsing of the cone-beam CT radiation source 204. In addition, it should also be appreciated the control system of the flat panel imager 206 allows an external synchronization signal (from the computer 220) to initiate the readout of a frame. This allows the user to externally control when the imager will acquire an image.

In one embodiment, a command processor module 225 manages the receptor module, processes the digital video, and provides interfaces to other components of the simulator 100. The command processor module 225 may include a microcontroller-based, single board computer running a real-time operating system with acquisition, control, and interface software. Also, included in the command processor may be a high-speed digital video interface card, a dedicated image processor card to perform real-time image corrections, a system interface card, and a parallel output to transmit image data to an external image processor and display. Scan-converted digital and analog video may also be provided.

The captured cone-beam CT image projection data may be delivered and stored to a computer 220. As shown in FIG. 1, the computer 220 connects to the simulator 100 and the command processor 225 via communications network 240. The computer 220 may control the synchronized movement of the simulator 100 including the rotatable gantry 202, the cone-beam CT radiation source 204, imager 206, and the treatment couch 218. Specifically, the computer 220 may be used by an oncologist to display image projection data on a monitor 222, control the intensity of the cone-beam CT radiation source 204, and control the gantry angle.

The cone-beam CT image projection data may also be transferred to a cone-beam CT reconstruction computer 221 that includes software designed to achieve rapid cone-beam CT image generation. The computer 221 can merge or reconstruct the image data into a three-dimensional representation of the patient and target volume. In one embodiment, cone-beam CT reconstruction software may allow for full-cone and partial-cone input data that can produce cone-beam CT images (e.g., approximately 26 to 48 cm diameter) at a specific source-to-imager distance (e.g., 140-150 cm). In addition, in this way, the clinical simulator machine 100 and cone-beam reconstruction software may also allow for large diameter (e.g., approximately 48 cm) axial image volumes.

In one embodiment, the cone-beam CT reconstruction software may transform the image projection data into volumetric CT image data. The volumetric CT image data may include full-fan and/or partial cone image data to reconstruct head size (e.g. 26 cm diameter×17 cm length) and body size (e.g. 48 cm diameter×15 cm length) volumes. For example, the partial-cone method may be used to obtain body size scans when the flat panel imager is not long enough to image the full body in each projection. If the 15 or 17 cm axial section is not wide enough and therefore does not cover sufficient anatomical volume, then multiple scans can be performed. For example, in the two scan case, the patient may be moved axially by 15 or 17 cm couch movements between scans and the reconstructed image volumes may then be merged to provide a 30 to 34 cm axial view.

In one embodiment, prior to reconstruction, the image projection data is preprocessed to account for x-ray beam and detector properties and the system electronic and geometric properties. The algorithm and its implementation is similar to that used in single slice computer tomography in reconstruction of fan beam data obtained with a one-dimensional detector. For partial cone beam reconstruction, the partial cone image projection data is extended to full cone beam image data and then reconstructed using a full cone beam reconstruction algorithm well known to those of ordinarily skill in the art, such as, for example, the Feldkamp cone beam reconstruction technique. It should be understood that the extension of the partial cone beam image data is performed using techniques similar to those used for the extension of partial fan data in well known single slice fan beam computer tomography.

In one embodiment, using the shape and distance data determined from the generated dimensional representation, the target volume may be automatically identified by the computer system 221 and/or by the inspection of an oncologist. The identified target volume may be applied to a radiotherapy planning computer system 220, which creates a treatment plan to be implemented by a clinical treatment machine. The visualization of the data along arbitrary planes, e.g. sagital, coronal, axial, beams eye view, etc., can be displayed to assist the oncologist. To further enhance the visualization, averaging of volume image data perpendicular to the plane of view, i.e. rectangular voxels may be used.

Figure 3:
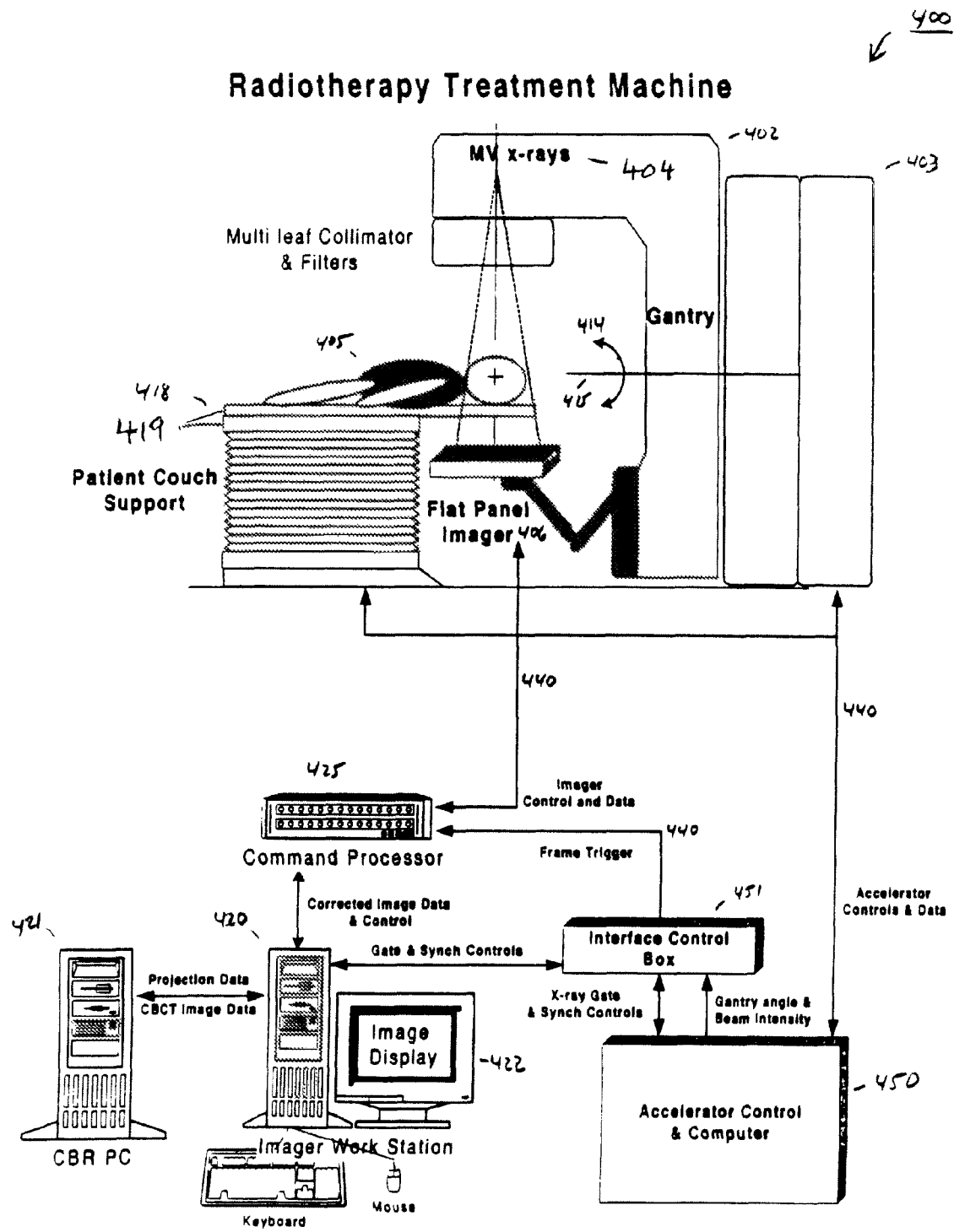
FIG. 3 is a side view of one embodiment of a clinical treatment machine.

FIG. 3 is a side view of one embodiment of a clinical treatment machine 400 that may implement the treatment plan generated by the simulator 100 and treatment planning computer 220. The clinical treatment machine 400 includes a rotatable gantry 402 pivotably attached to a drive stand 403. A cone-beam CT radiation source 404 and a flat panel imager 406 oppose each other and are coupled to the rotatable gantry 402. In one embodiment, the cone-beam CT radiation source 404 is a megavoltage (MV) radiation source generally in the 4 to 25 MV energy range, for example, at 6 MV.

A treatment couch 418 is positioned adjacent to the gantry 402 to place the patient and the target volume within the range of operation for the radiation source 404 and the imager 406. The couch 418 can be capable of translating in multiple planes plus angulation for positioning and re-positioning the patient 405 and therefore the target volume.

The gantry 402 can rotate 414 about an isocenterline 415 to place the cone-beam CT radiation source 404 and imager 406 at any position 360 degrees around the target volume. The resulting megavoltage cone-beam CT image data can then be used to tailor a dose of therapeutic radiation based on at least the generated pre-defined treatment plan.

Figure 4:
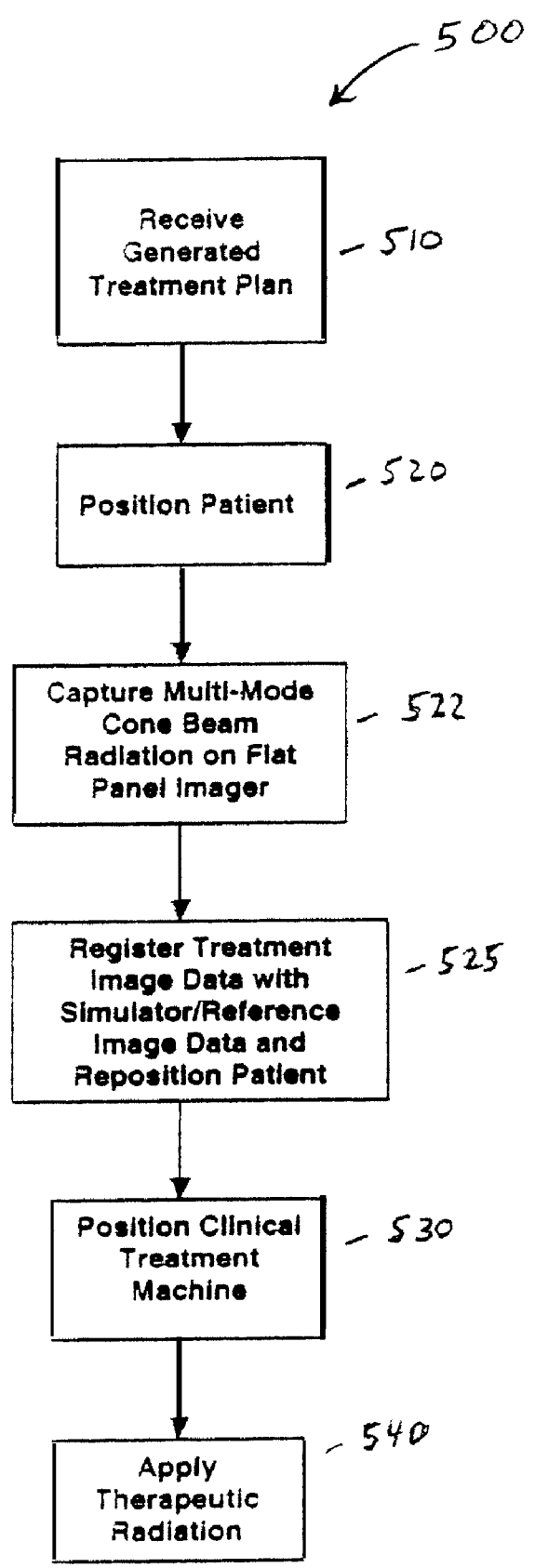
FIG. 4 illustrates a process flow of one embodiment of a method for implementing a treatment plan.

FIG. 4 is a process diagram of one embodiment of a method for implementing a treatment plan. At block 510, an accelerator control computer 450 is provided with the treatment plan generated from the clinical simulator machine 100 for a specific patient. For example, the treatment plan may provide initial targeting information about the target volume. At block 520, a patient is placed on the treatment couch 418 and the couch 418 is positioned relative to the clinical treatment machine 400. At block 522, multi-mode cone beam radiation from the radiation source 404 is captured by the imager 406 to generate images of the target volume. At block 525, the captured image data can be compared/registered with the simulator or other reference images to determine the patient repositioning required, if any, before treatment. Image data can also be taken without repositioning to determine the random and systematic errors in treatment position, if any. At block 530, the gantry 402 is rotated around the patient 405 to a treatment position based on the generated treatment plan. At block 540, a therapeutic radiation dose is applied to the target volume from the cone-beam CT radiation source 404 based on the generated treatment plan. The cone-beam CT radiation source 404 also impinges the flat-panel imager 406 with radiation. In this way, the flat panel imager 406 may provide verification that the target volume is properly targeted. The process 500 may be repeated until the treatment session is complete.

The flat panel imager 406 is similar to the flat panel imager 206 including the corresponding interconnects with a command processor module 425, a computer 420, a monitor 422, and a cone-beam reconstruction computer 421, corresponding with the command processor module 225, the computer 220, a monitor 422, and the cone-beam reconstruction computer 221, as described above. However, in one embodiment, the flat panel imager 406 may have its electronics unfolded from beneath the imager 406 and the input screen coating may be thicker (e.g., 9 mm vs. 0.6 mm). An example of a flat panel imager that may be used in the present invention is described in U.S. patent Ser. No. 10/013,199, now U.S. Pat. No. 6,800,898 B1, filed on Nov. 2, 2001, assigned to the assignee of the present invention and incorporated herein by reference.

The imager 406 may also interface with an accelerator interface control box 451. The accelerator interface control box 451 interfaces with an accelerator control computer 450 to provide synchronization and gated control between the imager 406 and the cone-beam CT radiation source 404 during treatment based on the generated treatment plan. As shown in FIG. 3, box 451, processor 425, and computer 450 connect to simulator 400 via communications network 440. This allows single or multiple beam pulse images that are not affected by accelerator noise during readout.

In one embodiment, the accelerator interface control box 451 includes a timing interface. The timing interface coordinates acquisition by the flat panel imager 406 and pulsing of the cone-beam CT radiation source 404. With this interface, as little as one radiation pulse (0.028 cGy at the isocenter) can be used to form projection images.

In one embodiment, the timing interface includes a National Instruments PCI 6602 data acquisition card from National Instruments Corporation of Austin, Tex. USA, that contains hardware and firmware for counting and timing pulses; computer software that provides control logic; and a user interface for the interface system. Alternatively, other cards may also be used.

A master clock signal is derived from a sync signal of the cone-beam CT radiation source 404, which may operate at 360 pulses/s (6 MV) or 180 pulses/s (15-18 MV), according to one embodiment. Using a counter on the National Instruments PCI 6602 card, the sync signal is divided down to produce a master clock, and hence are timed relative to the production of cone-beam CT radiation pulses from the cone-beam CT radiation source 404.

The master clock may be used to generate two control pulses, one that gates the cone-beam CT radiation source 404 on and off and the other that triggers the flat panel imager 406. In one embodiment, the frequency of these pulses is user selectable, and may be any value below 30 pulses/sec. The relative timing of the two pulses may also be user selectable. When the flat panel imager 406 is triggered there is a period, while the image is being read out (half a frame time) during which no beam from the cone-beam CT radiation source 404 is desired. A user can enter the appropriate delay that will prevent irradiation during the frame readout period of the imager. The length of the gate pulse of the cone-beam CT radiation source 404 is also user selectable. By adjusting the width of the gate pulse, the user can control the number of beam pulses emitted by the cone-beam CT radiation source 404 during each gate pulse.

It should be appreciated that the MV cone-beam CT flat panel imager 406 has a high quantum efficient 9 mm thick CsI:Tl screen (e.g., approximately 10% efficient at 6 MV), which preserves spatial resolution and minimizes dose to the patient by at least a factor of 5 over a standard 1 mm thin copper plate and less than 1 mm GOS (gadolinium oxysulfide) screens used in standard flat panel and screen-camera portal imaging. Therefore, images with as low as one 6 MV accelerator beam pulse (e.g., 0.028 cGy) per frame may be collected. In addition, a low patient dose of 8 to 16 cGy per cone-beam CT data set may be yielded for 300 to 600 CT image frames or projections per data set. The lower dose of the MV cone-beam CT radiation allows for more frequent use on each patient during the typical 30 to 37 fractionated treatment sessions. Moreover, reduced spatial resolution on the MV cone-beam CT scans can be afforded for faster processing time using the cone-beam reconstruction software on the CBR computer 421 to achieve rapid image generation.

It should be appreciated that a separate kV cone-beam CT radiation source (not shown) and another opposing flat panel imager (as described above on the simulator but not shown here) may also be coupled to the gantry 402 to perform a diagnostic cone-beam CT scan. For example, the kV cone-beam CT radiation source and opposing flat panel imager may be coupled to the treatment machine gantry 402 at an off axis of e.g. forty-five or ninety degrees from the MV cone-beam radiation source 404 and opposing imager 406. As before, software in the computers 420 and/or 421 may generate the three-dimensional representation of the patient anatomy and target volume from the cone-beam CT image data provided by the kV radiation source. The clinical treatment machine 400 may use the kV cone-beam CT image data to make any necessary adjustments to the treatment plan based on identified movement of the target volume or to determine the amount of patient repositioning required by the treatment couch 418 or collimator movements. In this way, the kV cone-beam CT radiation source and flat panel imager share a common axis of rotation with the MV cone-beam CT radiation source 404 and provide additional information for aligning the patient to the generated simulation treatment plan.

It should also be appreciated that in this way, either the clinical simulator machine 100 and/or the clinical treatment machine 400 diagnostic cone-beam CT image data can be used as a reference for applying the MV radiation beams.

It should also be understood that it is not necessary for the therapeutic radiation to be applied from the exact position(s) where any of the previously generated CT images were taken since the computer software can provide virtual two-dimensional representations for any desired radial location in-between the images.

It should be understood that although the clinical treatment machine 400 has been described as having a cone-beam radiation source, in alternative embodiments beam shaping, along with intensity modulation, may also be implemented based on the generated treatment plan by directing a therapeutic beam through a dynamic multileaf collimator. The multileaf collimator may include a series of stacked metal shims having a center of shim pairs where each shim of the pairs may be individually moved to create a shaped opening capable of shaping the therapeutic beam. To be effective, the radiation field should be large enough to radiate the entire tumor while at the same time minimize radiating healthy tissue. The collimator may be dynamic in that the shims can rapidly move to reshape the beam, which results in blocking the therapeutic beam from striking certain areas of the target volume based on the treatment plan. Such dynamic shaping may result in different areas of the tumor receiving different amounts of radiation over the time that a radiation dose is applied.

It should be appreciated that more or fewer processes may be incorporated into the methods illustrated in FIGS. 2 and 4 without departing from the scope of the invention and that no particular order is implied by the arrangement of blocks shown and described herein. It further will be appreciated that the method described in conjunction with FIGS. 2 and 4 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the terms "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or produce a result.

It should be appreciated that a clinical simulation machine having a cone-beam radiation source and flat-panel imagers, as described, allows for identification of a target volume via fluoroscopic, radiographic, and cone-beam CT imaging. In this way, the generation of the treatment plan via the clinical simulation machine prior to the application of therapeutic radiation, increases the accuracy of treating the tumor target. Furthermore, embodiments of the invention as described above may capture images while the gantry is continuously rotating versus traditional systems that stop and shoot every, approximately, four degrees around the patient, thereby further lessening the time for completion.

It should also be appreciated that the cone-beam volumetric reconstruction software can utilize image projection data at non-uniformly spaced gantry angles. Thus the data collection does not require a precise gantry speed of rotation. There is a normalizing detector at the radiation source, which is used to correct for system output variations. In one embodiment, the support arms for the images 206 and 406 are sufficiently precise in mechanical stability during gantry rotation that no compensating spatial corrections are required.

Although the present invention has been described with reference to specific exemplary embodiments, it will be evident that various modifications and changes may be made to these embodiments without departing from the broader scope of the invention as set forth in the claims. Accordingly, the specification and drawings are to be regarded in an illustrative rather than a restrictive sense.

What is claimed is:
1. An apparatus, comprising:
  logic configured to modify a treatment plan for a target volume, the logic comprising at least one of hardwired logic and a programmable computer component;
  a rotatable gantry;

a cone-beam radiation source coupled to the rotatable gantry; and a flat-panel imager coupled to the rotatable gantry, wherein the flat-panel imager is operable to capture image projection data to generate cone-beam computed tomography (CT) volumetric image data capable of being used by the logic to modify a treatment plan for a target volume.

2. The apparatus of claim 1 wherein the flat-panel imager includes an amorphous silicon sensor array capable of fluoroscopic imaging, radiographic imaging, and cone-beam CT imaging.

3. The apparatus of claim 2, wherein the cone-beam CT radiation source is a kilovoltage radiation source, and the flat-panel imager includes a cesium iodide scintillator for kilovoltage imaging.

4. The apparatus of claim 3, wherein the scintillator includes cesium iodide crystals coated with a reflective powder and epoxy mixture in a large matrix for megavoltage imaging.

5. The apparatus of claim 1, further comprising:
a computing unit, coupled to the rotatable gantry via a communications network, to store the image projection data captured by the flat-panel imager, wherein the computing unit generates the treatment plan based on the image projection data.

6. The apparatus of claim 1, further comprising a translatable treatment couch coupled to the rotatable gantry via a communications network, wherein the translatable treatment couch is capable of movement in three planes plus angulation.

7. The apparatus of claim 1, wherein the rotatable gantry continues to rotate while capturing image projection data.

8. The apparatus of claim 1, further comprising a megavoltage radiation source to radiate the target volume with between 4 and 25 mega-volts of radiation.

9. The apparatus of claim 1, further comprising a radiation simulation system comprising said gantry, said radiation simulation system comprising logic configured to determine a patient position or a radiation treatment system comprising said gantry, said radiation treatment system comprising logic configured to implement a treatment plan.

10. The apparatus of claim 1, further comprising logic configured to generate fluoroscopic or cone-beam computed tomography (CT) volumetric image data, wherein the imager captures fluoroscopic or cone-beam CT imaging image projection data be used by the logic configured to generate fluoroscopic or cone-beam computed tomography (CT) volumetric image data.

11. The apparatus of claim 1, further comprising:
a computing unit coupled to the rotatable gantry to generate a treatment plan for a clinical treatment machine based on the cone-beam volumetric image data, and to transfer the treatment plan to the clinical treatment machine, wherein the clinical treatment machine implements the treatment plan.

12. The apparatus of claim 1, wherein the programmable computer component comprises a processor.

13. A method to perform a clinical treatment, comprising:
using a clinical simulator machine to capture image projection data from a flat-panel imager for generating cone-beam computed tomography (CT) volumetric image data capable of being used by logic of the clinical simulator machine configured to modify a treatment plan for a clinical treatment machine;
emitting a cone-beam from a radiation source;
transmitting at least a portion of the cone-beam through a target volume;
providing a treatment plan;
modifying said treatment plan for a clinical treatment machine using said logic and based on the cone-beam volumetric image data;
transferring the treatment plan to the clinical treatment machine, wherein the clinical treatment machine implements the treatment plan; and
treating a patient according to the treatment plan including providing synchronization and gate control between the imager and a therapeutic radiation beam during treatment, wherein treating includes coordinating acquisition by the flat panel imager and pulsing by a therapeutic radiation source.

14. The method of claim 13, wherein the clinical simulator machine includes the cone-beam radiation source, the cone-beam radiation source including a kilovoltage radiation source at a position opposed to the imager, and further comprising:
using the treatment plan to instruct the clinical treatment machine to at least adjust a megavoltage therapeutic radiation source into position to align the target volume with a therapeutic radiation beam, and
radiating the target volume with a megavoltage radiation source of the clinical treatment machine.

15. The method of claim 13, further comprising:
deriving a master clock signal from a synchronization signal of the cone-beam radiation source;
using the master clock to generate a first control pulse to gate the cone-beam radiation source on and off and a second control pulse to trigger reading of an image from the imager;
selecting a timing of the first control pulse as compared to the second control pulse to read out the image while the cone-beam radiation source is off.

16. The method of claim 13, wherein the image projection data is generated from the flat-panel imager capturing radiation from a cone-beam computed tomography radiation source passing through a target volume, and capturing comprises capturing the image projection data at a frame rate in the range of 15-30 frames per second.

17. The method of claim 13, wherein the image projection data is fluoroscopic image projection data or cone-beam CT imaging image projection data.

18. A method to perform a clinical treatment, comprising:
using a clinical simulator machine to capture image projection data from a flat-panel imager for generating cone-beam computed tomography (CT) volumetric image data capable of being used by logic of the clinical simulator machine configured to modify a treatment plan for a clinical treatment machine;
emitting a cone-beam from a radiation source;
transmitting at least a portion of the cone-beam through a target volume;
providing a treatment plan;
modifying said treatment plan using said logic;
continuing to rotate a gantry on which the imager is mounted while capturing image projection data; and
one of capturing radiation at non-uniformly spaced angles with respect to a rotation, and changing the speed of rotation of the gantry during a rotation.

19. A method to perform a clinical treatment, comprising:
using a clinical simulator machine to capture first image projection data from a flat-panel imager for generating cone-beam computed tomography (CT) volumetric image data capable of being used by logic of the clinical simulator machine configured to modify a treatment plan for clinical treatment of a target volume;

radiating a target volume with a megavoltage radiation source;

capturing second image projection data produced using the megavoltage radiation source; and, providing a treatment plan;

modifying said treatment plan using said logic.

20. The method of claim 19, wherein the megavoltage radiation source radiates the target volume with a cone beam, and the second image projection data produced using the megavoltage radiation source comprises data produced using cone beam CT volumetric data.

* * * * *

UNITED STATES PATENT AND TRADEMARK OFFICE
CERTIFICATE OF CORRECTION

| | | |
|---|---|---|
| PATENT NO. | : 8,116,430 B1 | Page 1 of 1 |
| APPLICATION NO. | : 11/891505 | |
| DATED | : February 14, 2012 | |
| INVENTOR(S) | : Shapiro et al. | |

It is certified that error appears in the above-identified patent and that said Letters Patent is hereby corrected as shown below:

Title Page, Item (75) Inventors, should read

-- (75)   Inventors: Edward G. Shapiro, Menlo Park, CA (US); Edward J. Seppi, Portola Valley, CA (US); John M. Pavkovich, Palo Alto, CA (US); Stanley W. Johnsen, Palo Alto, CA (US); Richard E. Colbeth, Los Altos, CA (US) --.

Signed and Sealed this
Twenty-first Day of June, 2016

Michelle K. Lee
*Director of the United States Patent and Trademark Office*